(12) United States Patent
Shabanov et al.

(10) Patent No.: US 7,161,026 B1
(45) Date of Patent: Jan. 9, 2007

(54) METHOD OF PREPARATION OF METHYL-BENZYL-KETONE

(75) Inventors: Alimamed Latif Shabanov, Baku (AZ); Elmira Mamedem Ramazanova, Baku (AZ)

(73) Assignee: Property Development Corporation International, Ltd, Inc., Baku (AZ)

( * ) Notice: Subject to any disclaimer, the term of this patent is extended or adjusted under 35 U.S.C. 154(b) by 0 days.

(21) Appl. No.: 11/177,760

(22) Filed: Jul. 8, 2005

(51) Int. Cl.
*C07C 51/16* (2006.01)

(52) U.S. Cl. ..................................................... 562/409
(58) Field of Classification Search ................. 562/409
See application file for complete search history.

(56) References Cited

U.S. PATENT DOCUMENTS

| | | | |
|---|---|---|---|
| 3,558,690 | A | 1/1971 | Sallmann et al. |
| 3,651,101 | A | 3/1972 | Boldt et al. |
| 3,870,751 | A | 3/1975 | Houlihan et al. |
| 3,968,124 | A | 7/1976 | Mizutani et al. |
| 4,125,732 | A | 11/1978 | McEvoy et al. |
| 4,237,314 | A | 12/1980 | Sheng et al. |
| 5,756,426 | A | 5/1998 | Ziegler et al. |
| 5,756,858 | A | 5/1998 | Lantzsch et al. |
| 6,395,921 | B1 | 5/2002 | Marhold et al. |
| 6,531,597 | B1 | 3/2003 | Hoffmann-Emery et al. |

FOREIGN PATENT DOCUMENTS

| | | |
|---|---|---|
| EP | 1207148 A1 | 11/2001 |
| JP | 55-130949 A2 | 10/1980 |
| JP | 57-112352 A2 | 7/1982 |
| WO | 58-206542 A2 | 12/1983 |
| WO | WO 0123346 A2 | 4/2001 |

OTHER PUBLICATIONS

Phenylsodium Route to Phenylacetic Acid and Dimethyl Phenylmalonate John F Nobis and Louis F Moormeier Industrial and Engineering Chemistry vol. 46, No. 3 pp. 539-544.*

A.N. Nesmeyanov, T.V. Talayeva, K.A. Kocheshkov, "Method of elecmento-organic chemistry" Nauka Publishers, Moscow, 1971, pp. 951-992.

Gilmann, Henry, et al, "Benzylalkali Compouds," J. Am. Chem. Soc., vol. 62, 1514 (1940).

Nobis, John, et al, "Phenylsodium Route to Phenylacetic Acid and Dimenthyl Phenylmalonate," Indus. Eng. Chem. vol. 46, No. 3, 539 (1954).

Morton, Avery, et al, "Condensations by Sodium. VII. Solvent Exchange Reactions, . . . ," J. Am. Chem. Soc., vol. 58, 2599 (1936).

Morton, Avery et al, "Condensations by Sodium. XII. Mechanism of Formation of Phenylmalonic Acid . . . ," J. Am. Chem. Soc., vol. 60, 1426 (1938).

R.L. Letsinger, "The Preparation of Optically Active Hydrocarbons by the Wurtz Reaction," J. Am. Chem. Soc., vol. 70, 406 (1948).

Gilman, Henry, and H.A. Pacevitz, "The Carbonation of Organoalkali Compounds," J. Am. Chem. Soc., vol. 62, 1301 (1940).

Hansley, V.L., "Sodium Reduction of Fatty Acid Esters," Indus. Eng. Chem., vol. 39, 55 (1947).

Pacevitz, H.A., "Laterial Organoalkali Compounds," Chem. Abstracts, vol. 36, 4475 (1942).

Rhodium, "Synthesis of Phenylacetic Acid" http://www.rhodium.ws/chemistry/phenylacetic.html, Nov. 6, 2004.

* cited by examiner

*Primary Examiner*—Samuel A Barts
*Assistant Examiner*—Lalitha Nagubandi
(74) *Attorney, Agent, or Firm*—James J. Murphy; Thompson & Knight, LLP

(57) ABSTRACT

A process for producing phenylacetic acid is provided. The process includes combining sodium, chlorobenzene, toluene, and a catalyst to form a suspension. This suspension is mixed to form phenylsodium. Upon boiling, the suspension forms benzylsodium. The suspension is then carbonized and acidified to form phenylacetic acid.

17 Claims, 1 Drawing Sheet

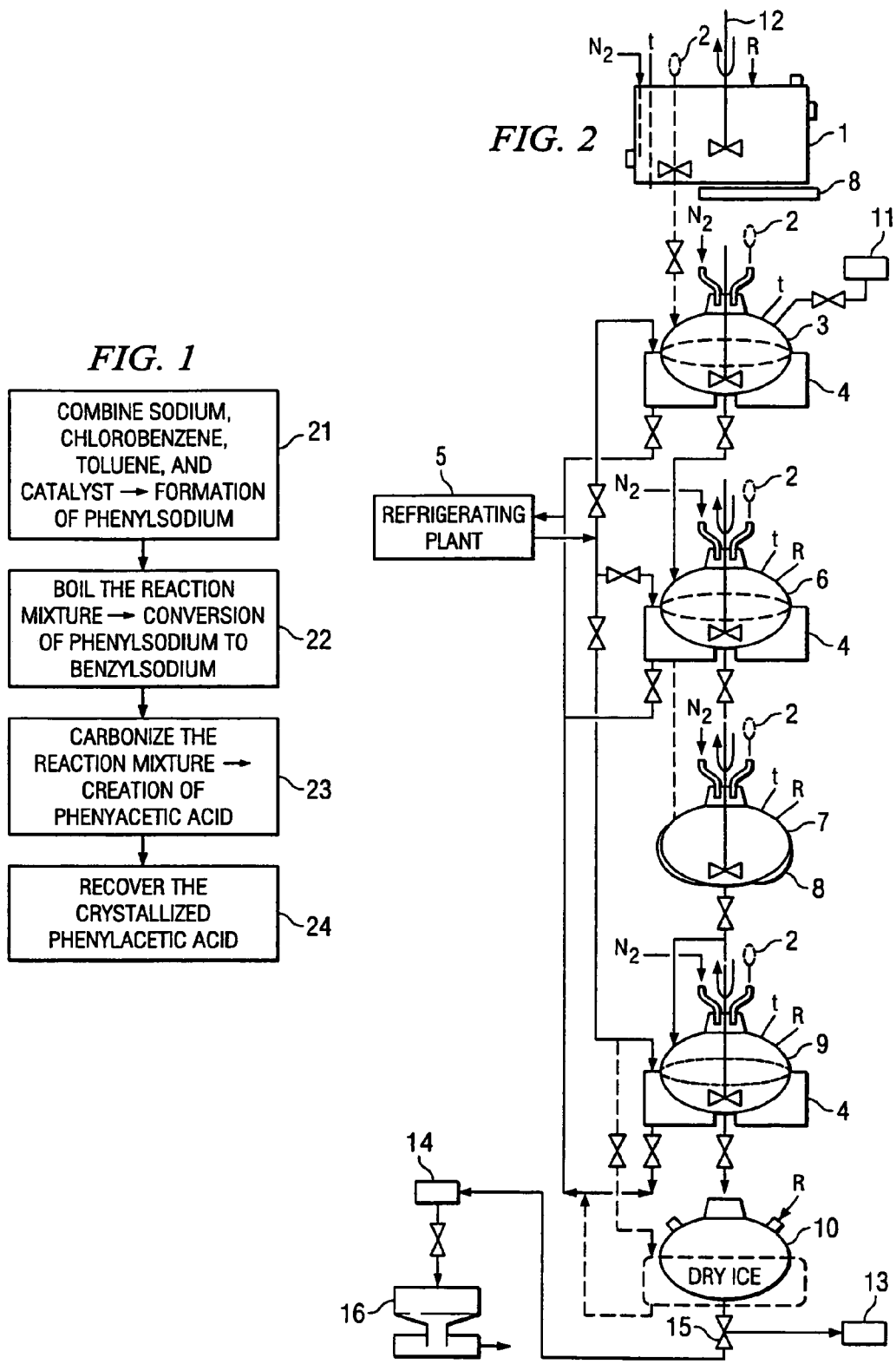

METHOD OF PREPARATION OF METHYL-BENZYL-KETONE

BACKGROUND OF THE INVENTION

1. Field of the Invention

The present invention relates to a process for the production of phenylacetic acid. More specifically, the invention relates to the formation of phenylsodium from a mixture of chlorobenzene, sodium, toluene, and catalyst with further catalytic conversion of phenylsodium to benzylsodium. The invention further relates to a process whereby the benzylsodium is used as a precursor to create phenylacetic acid.

2. Description of Related Art

Current processes for the production of phenylacetic acid using sodium-toluene, and chlorobenzene as precursors are slow and do not provide a high yield. Non-catalytic methods are not cost-effective, stable methods for the production of phenylacetic acid because of the long duration of the benzylchloride metalation, benzylsodium production, and carboxylation stages. This makes the current processes expensive and time-consuming and therefore unsuited for continuous-process industrial production of phenylacetic acid.

Further, current processes for the production of phenylacetic acid can be used only under laboratory conditions aiming at producing small amounts of the product. Further, the purity of the product obtained is not high due to the formation of byproducts (phenylmalonic acid, etc.), which requires supplementary purification. This creation of byproducts reduces output to 65–70%. Further, current processes are environmentally unfriendly and are not capable of being carried out in a stainless steel reactor. Thus, the current processes for the production of phenylacetic acid are not economically expedient and fail to be useful as continuous methods of phenylacetic-acid industrial production.

A need exists, therefore, for a process that reduces the process time and increases the yield of phenylacetic acid, thereby providing a commercially-viable method for the production of phenylacetic acid.

All references cited herein are incorporated by reference to the maximum extent allowable by law. To the extent a reference may not be fully incorporated herein, it is incorporated by reference for background purposes and indicative of the knowledge of one of ordinary skill in the art.

BRIEF SUMMARY OF THE INVENTION

The problems presented in current processes for the production of phenylacetic acid from sodium, toluene, and chlorobenzene precursors are solved by the methods of the present invention. This invention makes possible an industrially-viable, continuous process for the production of high-purity phenylacetic acid (95–99%), which maintains a stable yield (90–95%), by reducing the time for the phenylsodium, benzylsodium, and carbonization processing stages due to the presence of a catalyst.

In accordance with one embodiment of the present invention, a special-purpose high-speed mixer is used to create a suspension of sodium in toluene. A catalyst is added thereby catalyzing the dissolution of sodium particles from the solid phase into the toluene layer and accelerating the rate of the reaction of sodium suspended in toluene with chlorobenzene, resulting in the high-yield formation of phenylsodium according to the formula I. The continuity of production is maintained due to catalytic action of macroheterocycling ligands.

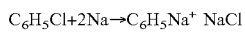

Further, the catalyst is used to accelerate the reaction rate and increase the yield in the conversion of phenylsodium to benzylsodium according to the formula II. By boiling the resulting solution in the presence of the catalyst, phenylsodium is transformed into benzylsodium at a rate approximately 1.5 times greater than that in non-catalytic method.

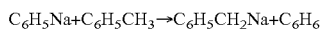

The catalyst is preferably a criptand or crown compound. Preferably, 0.0005–0.001% catalyst, calculated on sodium, is used in the process.

Under further processing, the benzylsodium is carbonized to form phenylacetic acid. Preferably, dry ice is used to carry out the carbonation. By pouring out a thin jet of the reaction mixture into crushed dry ice, phenylacetic acid sodium salt is formed with further conversion into phenylacetic acid by hydrolysis and acidification.

The invented process reduces the phenylacetic-acid production time by 50% when compared to the current processes and addresses each of the other problems found with current processes.

Other objects, features, and advantages of the present invention will become apparent with reference to the drawings and detailed description that follow.

BRIEF DESCRIPTION OF THE DRAWINGS

For a more complete understanding of the present invention, and the advantages thereof, reference is now made to the following descriptions taken in conjunction with the accompanying drawings, in which FIG. 1 is a block diagram of a representative embodiment of the present invention.

FIG. 2 is a schematic flow diagram illustrating an exemplary process embodying the present invention.

DETAILED DESCRIPTION OF THE PREFERRED EMBODIMENT

In the following detailed description of the preferred embodiments, reference is made to the accompanying drawings which form a part hereof, and in which is shown by way of illustration specific preferred embodiments in which the invention may be practiced. These embodiments are described in sufficient detail to enable those skilled in the art to practice the invention, and it is understood that other embodiments may be utilized and that logical chemical and mechanical changes may be made without departing from the spirit or scope of the invention. To avoid detail not necessary to enable those skilled in the art to practice the invention, the description may omit certain information known to those skilled in the art. The following detailed description is, therefore, not to be taken in a limiting sense, and the scope of the present invention is defined only by the appended claims.

Referring to FIG. 1, there are four basic steps to the inventive phenylacetic acid production process. Some of the basics of the process can be found in Gilman, Henry, et al, "Benzylalkali Compouds," J. Am. Chem. Soc., Vol. 62, 1514 (1940); Nobis, John, et al, "Phenylsodium Route to Phenylacetic Acid and Dimenthyl Phenylmalonate," Indus. Eng. Chem. Vol. 46, No. 3, 539 (1954); Morton, Avery and Ingenuin Hechenbleikner "Condesations by Sodium. VII.

Solvent Exchange Reactions, Preparation of Phenylmalonic Acid, and Comments on Some Mechanisms of Reactions which Employ Sodium," J. Am. Chem. Soc., Vol. 58, 2599 (1936); Morton, Avery, et al, "Condensations by Sodium. XII. Mechanism of Formation of Phenylmalonic Acid and the Syntheses of Butyl- and Phenylmalonic Acids from Monocarboxylic Acids," J. Am. Chem Soc., Vol. 60, 1426 (1938); R. L. Letsinger, "The Preparation of Optically Active Hydrocarbons by the Wurtz Reaction," J. Am Chem. Soc., Vol. 70, 406 (1948); Gilman, Henry, and H. A. Pacevitz, "The Carbonation of Organoalkali Compounds," J. Am. Chem. Soc., Vol. 62, 1301 (1940); Hansley, V. L., "Sodum Reduction of Fatty Acid Esters," Indus. Eng. Chem., Vol. 39, 55 (1947); and Pacevitz, H. A., "Lateral Organoalkali Compounds," Chem. Abstracts, Vol 36, 4475 (1942); incorporated herein by reference.

First, an alkali metal, a phenyl halide, a solvent, and a catalyst are combined. An example of this is combining sodium, chlorobenzene, toluene, and a catalyst. Under proper processing conditions, described herein, the sodium and chlorobenzene react to form phenylsodium. Second, this reaction mixture is boiled, which causes the phenylsodium and toluene to react and form benzylsodium. Third, the reaction mixture is carbonized, preferably over dry ice, hydrolyzed, and acidified, which leads to the formation of phenylacetic acid. Finally, the phenylacetic acid is crystallized and recovered from the reaction mixture.

In more detail, referring to FIG. 2, metallic sodium and toluene are added to a preliminary reactor 1 for sodium disintegration. A special-purpose, high-speed mixer 12, preferably capable of achieving at least 10,000 revolutions per minute, is switched on to crush the sodium and to produce a sodium-in-toluene suspension. Preferably, the mixer need only be used for around 1–1.5 minutes. The suspension is then cooled down to around 25–30° C.

A solution containing equivalent amounts of chlorobenzene and dry toluene with around 0.0005–0.001% catalyst calculated on sodium are contained in a chlorobenzene tank 11. Effective catalysts are cryptands and crown compounds, such as crown ethers. Preferably, the macrocyclic-catalyst will have a cavity size which corresponds to the ion radius of sodium. The preferred catalysts are cryptand [2,2,2] and 16-crown-5. An equivalent amount of the solution from the chlorobenzene tank 11 is added to and mixed with the preliminarily prepared suspension of metallic sodium in toluene in the preliminary reactor 1. This mixture is transferred to a phenylsodium-conversion reactor 3 with the sodium particle size not to exceed 20–25 microns.

Alternatively, the solution from the chlorobenzene tank 11 can be added directly to the phenylsodium-conversion reactor 3 without premixing the solution with the suspension in the preliminary reactor 1. Another alternative is to add the chlorobenzene and catalyst to the preliminary reaction mixture in the preliminary reactor 11 prior to initial mixing.

For a phenylsodium-conversion reactor of 2 liter volume, the feed rate of the reagents to the phenylsodium-conversion reactor should be around 4.3 mol/hr. The reactor can have an external cooling jacket.

The temperature in the phenylsodium-conversion reactor 3 is maintained in the range of around 2740° C. by regulating the reagent feed rates and the external cooling of the phenylsodium-conversion reactor 3. The preferred amount of catalyst is 0.001% based on sodium. More than 0.001% catalyst can be used, but the economics for larger amounts of catalyst are not as good as for the preferred amount. All process steps should be carried out in an inert atmosphere such as nitrogen. Generally, any dry gas may be used in this process.

Approximately every 10 minutes the suspension accumulated in the phenylsodium-conversion reactor 3 is transferred into a reserve tank 6 where mixing is continued. The temperature of the reserve tank 6 is maintained preferably at 30–40° C. Upon reaching a desired volume, the suspension in the reserve tank 6 is transferred to a benzylsodium-conversion reactor 7. The suspension is boiled in the benzylsodium-conversion reactor 7. Boiling is maintained for approximately 0.5–1.5 hours, preferably for 1.0–1.5 hours.

After boiling in the benzylsodium-conversion reactor 7, the prepared benzylsodium suspension is transferred to a cooling tank 9 where the benzylsodium suspension is cooled to 25° C. Following cooling in the cooling tank 9, the benzylsodium suspension is discharged by jet onto disintegrated dry ice in the carbonation reactor 10 and slowly mixed. Alternatively, liquid $CO_2$ may be used. The dry ice in the carbonation reactor 10 is in an amount of 20 fold mole excess based on benzylsodium.

After volatilization of the $CO_2$, the residue is hydrolyzed with water by mixing and cooling in the carbonation reactor 10. The volume of water used for hydrolysis is equal to 25–35% of the toluene volume.

The aqueous layer is then separated from the toluene layer and is acidified, preferably with hydrochloric acid. The pH is preferably lowered to a pH of approximately pH 2.

The phenylacetic acid is then crystallized and separated from the water. The phenylacetic acid prepared by the invented process has a melting temperature of 75–76° C.

1. Experiment:

4.7 g. of sodium, 30 ml of absolute toluene and 6 mg of catalyst are put into a stainless-steel preliminary reactor that has a mixer capable of mixing at 10,000 revolutions per minute, a heater, a backflow condenser, a viewing window, and a cooling jacket. All processes are carried out in a dry-nitrogen atmosphere. The reactor is heated up to the toluene boiling point Then the high-speed mixer is switched on for 1–1.5 minutes for sodium crushing.

The suspension is then cooled down to 25–30° C. and placed in a phenylsodium-conversion reactor. 5–8 ml of a chlorobenzene and toluene solution, made by mixing the 2 reagents in equal proportion with catalyst, is added to toluene-sodium suspension while mixing and cooling the reactor to 2740° C. The reaction begins immediately and black sediments of phenylsodium are generated in the reactor. The temperature of reaction mixture is kept at 2740° C. The chlorobenzene metallizing reaction takes approximately 1 hour.

The suspension of phenylsodium is taken from the pheynylsodium-conversion reactor to a reserve tank, where reaction is completed in a nitrogen atmosphere. In order to transform phenylsodium into benzylsodium, the contents of the reserve tank are placed into a benzylsodium-conversion reactor, where the suspension boils for 1–1.5 hours. While boiling, the solution's color gets brick-red and then black again.

Upon completion of the reaction, the hot solution is removed from the benzylsodium-conversion reactor and placed into a cooling tank. Then as soon as possible, the cooled reaction mass is poured into crushed dry ice in a carbonation reactor and mixed. When vaporization of the $CO_2$ is completed, 20 ml of water is added to the residue during cooling and mixing. The water layer is then separated and acidulated with hydrochloric acid to a pH around pH 2.

The generated sediment phenylacetic acid is separated by filtration in a vacuum-filter. 12.5 g. of phenylacetic acid (92%) with melting point 77° C. is produced. The results of other experiments are given in the Table 1.

TABLE 1

Experimental results of PhAA production in the absence and presence of catalyst respectively

| Time of boiling of phenylsodium in toluene, hr. | PhAA production in the absence of catalyst, % Rate of addition of toluene solution of chlorobenzene and toluene suspension of sodium, 4.3 mole/hr. | | | | PhAA yields in the presence of catalyst, % Rate of addition of toluene solution of chlorobenzene and toluene suspension of sodium, 4.3 mole/hr. | | | |
|---|---|---|---|---|---|---|---|---|
| | 2.5 | 3.5 | 4.3 | 5 | 2.5 | 3.5 | 4.3 | 5 |
| 0.5 | 16.2 | 18.9 | 27 | 33 | 66 | 74 | 75 | 70 |
| 1 | 34.6 | 40.5 | 48 | 54 | 83.5 | 90 | 94.5 | 89 |
| 2 | 42.8 | 44.8 | 52 | 58 | 83.4 | 89.8 | 93.7 | 86.7 |
| 3 | 52.5 | 60.4 | 62.5 | 69 | 80.8 | 90.6 | 90.3 | 85.9 |
| 4 | 49.6 | 58.4 | 66.5 | — | 76 | 87 | 88 | 80.8 |

The table shows that including a catalyst greatly increases phenylacetic-acid yield. The highest yield of the product is observed when the time of boiling in toluene equals 1 hour time. Further increase in boiling time causes a decrease in desired product yield. Also, the application of a catalyst improves the stability of the results.

It was also observed that the increase in catalyst amount to 0.001% leads to a rise in yield of the desired product. Further increases in catalyst amount do not generally give an increase of the desired product It should be apparent from the foregoing that an invention having significant advantages has been provided. Although the invention has been described with reference to specific embodiments, these descriptions are not meant to be construed in a limiting sense. Various modifications of the disclosed embodiments, as well as alternative embodiments of the invention, will become apparent to persons skilled in the art upon reference to the description of the invention. It should be appreciated by those skilled in the art that the conception and the specific embodiment disclosed might be readily utilized as a basis for modifying or designing other structures for carrying out the same purposes of the present invention. It should also be realized by those skilled in the art that such equivalent constructions do not depart from the spirit and scope of the invention as set forth in the appended claims.

It is therefore contemplated that the claims will cover any such modifications or embodiment that fall within the true scope of the invention.

We claim:

1. A process for producing phenylacetic add comprising:
    combining sodium, chlorobenzene, toluene, and a catalyst from the group consisting of criptands and crown compounds to form a suspension;
    mixing the suspension to form phenylsodium;
    boiling the suspension to form benzylsodium; and
    carbonizing and acidifying the suspension to form phenylacetic acid.

2. The process according to claim 1 wherein combining comprises;
    mixing sodium and toluene to form a sodium suspension and then adding the chlorobenzene and catalyst to the sodium suspension.

3. The process according to claim 1 wherein:
    the catalyst is cryptand [2,2,2].

4. The process according to claim 1 wherein:
    the catalyst is 16-crown-5.

5. The process according to claim 1 wherein:
    sodium has an ion radius and the catalyst chosen has a cavity size that corresponds to the ion radius of sodium.

6. The process according to claim 1 wherein:
    0.001% cryptand [2,2,2] calculated on sodium is added to the suspension as the catalyst.

7. The process according to claim 1 wherein:
    0.0005–0.001% catalyst calculated on sodium is added to the suspension as the catalyst.

8. The process according to claims 1 wherein:
    the process is carried out in an inert atmosphere.

9. The process according to claim 1 wherein:
    the process is carried out in an inert atmosphere.

10. The process according to claim 8 wherein:
    the inert atmosphere is nitrogen.

11. The process according to claim 1 further comprising;
    maintaining the temperature between 27–40° C. during mixing.

12. The process according to claim 1 further comprising:
    boiling the suspension for 0.5–1.5 hours to form phenylsodium.

13. The process according to claim 1 further comprising:
    carbonizing the suspension by jetting said suspension into $CO_2$.

14. The process according to claim 13 wherein:
    the $CO_2$ is crushed dry ice.

15. A process for producing phenylacetic acid comprising:
    combining an alkali metal, a phenyl halide, a solvent, and a catalyst from the group consisting of criptands and crown compounds.

16. A process for producing phenylacetic acid comprising:
    combining sodium, chlorobenzene, toluene, $CO_2$, an acid, and a catalyst from the group consisting of criptands and crown compounds, to form a suspension.

17. A process for forming phenylsodium comprising:
    combining sodium, toluene, and a catalyst from the group consisting of cryptands and crown compounds.

\* \* \* \* \*

UNITED STATES PATENT AND TRADEMARK OFFICE
CERTIFICATE OF CORRECTION

PATENT NO.        : 7,161,026 B1
APPLICATION NO. : 11/177760
DATED             : January 2, 2007
INVENTOR(S)       : Shabanov et al.

It is certified that error appears in the above-identified patent and that said Letters Patent is hereby corrected as shown below:

On the Title Page, Item (54) title should read -- METHOD OF PHENYLACETIC ACID PRODUCTION--.

Item (75) Inventors, the second inventor should read --Elmira Mamedemin Ramazanova--

Signed and Sealed this

Twenty-second Day of May, 2007

JON W. DUDAS
*Director of the United States Patent and Trademark Office*

UNITED STATES PATENT AND TRADEMARK OFFICE
CERTIFICATE OF CORRECTION

PATENT NO.       : 7,161,026 B1                                      Page 1 of 1
APPLICATION NO.  : 11/177760
DATED            : January 9, 2007
INVENTOR(S)      : Shabanov et al.

It is certified that error appears in the above-identified patent and that said Letters Patent is hereby corrected as shown below:

On the Title Page, Item (54) title should read -- METHOD OF PHENYLACETIC ACID PRODUCTION--.

Item (75) Inventors, the second inventor should read --Elmira Mamedemin Ramazanova--

This certificate supersedes Certificate of Correction issued May 22, 2007.

Signed and Sealed this

Twentieth Day of November, 2007

JON W. DUDAS
*Director of the United States Patent and Trademark Office*